Figure 1:
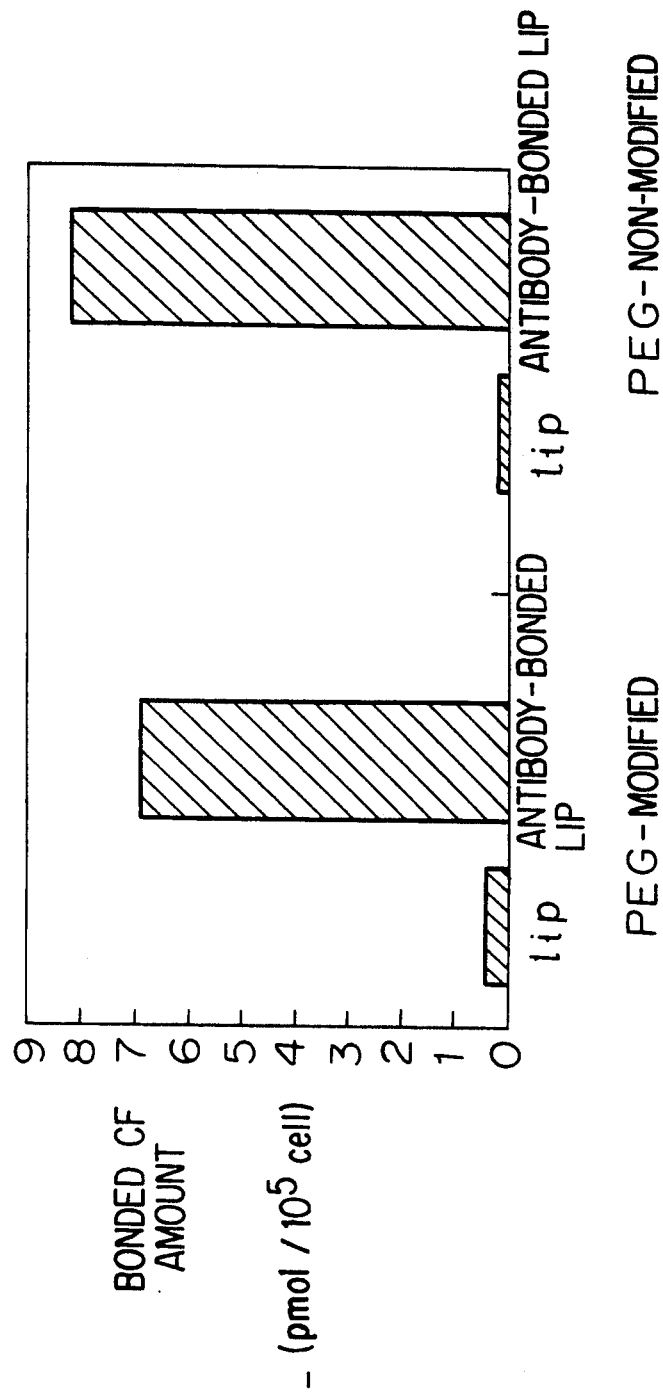

United States Patent [19]

Tagawa et al.

[11] Patent Number: 5,264,221
[45] Date of Patent: Nov. 23, 1993

[54] DRUG-CONTAINING PROTEIN-BONDED LIPOSOME

[75] Inventors: Toshiaki Tagawa, Yokohama; Saiko Hosokawa, Kawasaki; Kazuhiro Nagaike, Sagamihara, all of Japan

[73] Assignee: Mitsubishi Kasei Corporation, Tokyo, Japan

[21] Appl. No.: 886,846

[22] Filed: May 22, 1992

[30] Foreign Application Priority Data

May 23, 1991 [JP] Japan ................................ 3-118762

[51] Int. Cl.$^5$ .......................................... A61K 9/127
[52] U.S. Cl. ................................ 424/450; 428/402.2; 436/829; 935/54; 530/812
[58] Field of Search ............... 424/450, 417; 436/829; 428/402.2; 264/4.1; 530/402, 403, 810, 812; 935/54

[56] References Cited

U.S. PATENT DOCUMENTS 4,429,008 1/1984 Martin ................................ 424/450
5,059,421 10/1991 Loughrey et al. ................. 424/418

FOREIGN PATENT DOCUMENTS 0354855 2/1990 European Pat. Off.
9004384 5/1990 PCT Int'l Appl.

OTHER PUBLICATIONS

Allen et al BBA, 1066, p. 29, 1991.
Klibanov. FEBS 268, p. 235 1990.
Biochimica et Biophysica Acta, 1062, pp. 142–148, 1991, A. L. Klibanov, et al., "Activity of Amphipathic Poly(ethylene glycol) 5000 to Prolong the Circulation Time of Liposomes Depends on the Liposome Size and is Unfavorable for Immunoliposome Binding to Target".
FEBS Letters, vol. 284, No. 2, pp. 263–266, Jun., 1991, A. Mori, et al., "Influence of the Steric Barrier Activity of Amphipathic Poly(ethyleneglycol) and Ganglioside $GM_1$ on the Circulation Time of Liposomes and on the Target Binding of Immunoliposomes in Vivo".
Nature, vol. 288, pp. 602–604, Dec. 11, 1980, L. D. Leserman, et al., "Targeting to Cells of Fluorescent Liposomes Covalently Coupled with Monoclonal Antibody or Protein A".
The Journal of Biological Chemistry, vol. 257, No. 1, pp. 286–288, Jan. 10, 1982, F. J. Martin, et al., "Irreversible Coupling of Immunoglobulin Fragments to Preformed Vesicles".
The Journal of Biological Chemistry, vol. 255, No. 17, pp. 8015–8018, Sep. 10, 1980, A. Huang, et al, "Monoclonal Antibody Covalently with Fatty Acid".
Cancer Research, vol. 43, pp. 5328–5334, Nov., 1983, Y. Hashimoto, et al., "Antitumor Effect of Actinomycin D Entrapped in Liposomes Bearing Subunits of Tumor-Specific Monoclonal Immunoblobulin M Antibody[1]".
Cancer Research, vol. 47, pp. 4471–4477, Aug. 15, 1987, H. Konno, et al., "Antitumor Effect of Adriamycin Entrapped in Liposomes Conjugated with Anti-Human Alpha-Fetoprotein Monoclonal Antibody[1]".
FEBS Letters, vol. 268, No. 1, pp. 235–237, Jul., 1990, A. L. Klibanov, et al., "Amphipathic Polyethyleneglycols Effectively Prolong the Circulation Time of Liposomes".
Biochimica et Biophysica Acta, 1061, pp. 56–64, 1991, T. M. Allen, et al., "Uptake of Liposomes by Cultured Mouse Bone Marrow Macrophages: Influence of Liposome Composition and Size".
Biochimica et Biophysica Acta, 1066, pp. 29–36, 1991, T. M. Allen, et al., "Liposomes Containing Synthetic Lipid Derivatives of Poly(ethylene glycol) Show Prolonged Circulation Half-Lives in Vivo".
World Patent Index Latest, No. 89-335876.

Primary Examiner—Thurman K. Page
Assistant Examiner—G. S. Kishore
Attorney, Agent, or Firm—Oblon, Spivak, McClelland, Maier & Neustadt

[57] ABSTRACT

A drug-containing protein-bonded liposome comprising a liposome containing a drug and having maleimide residues on its surface, and a protein and residues of a compound having a polyalkylene glycol moiety, bonded via respective thiol groups to the maleimide residues.

15 Claims, 2 Drawing Sheets

DRUG-CONTAINING PROTEIN-BONDED LIPOSOME

The present invention relates to selective chemotherapeutic drugs for various diseases including cancer. More particularly, it relates to a drug-containing protein-bonded liposome.

A missile therapeutic agent whereby a drug can be concentrated at a required active site utilizing a specific reactivity of an antibody, is expected to be useful in various medical fields including a field of cancer treatment in view of its high level of effectiveness and low side effects. For realization of such a missile therapeutic agent, it is important to establish a technology for combining an antibody and a drug. Heretofore, it has been attempted to bond an antibody and a drug by a method wherein a drug is chemically modified for bonding i.e. a method wherein an antibody and a drug are directly bonded, or a method wherein they are bonded via a water-soluble polymer such as dextran. However, with these methods, problems have been pointed out that the amount of a drug which can be bonded per molecule of an antibody is small, and the activities tend to be reduced by the modification of a drug. On the other hand, as a means for transporting a drug in a large amount without modifying the drug, a method has been proposed wherein a drug is contained in a liposome and an antibody is bonded to the surface of the liposome. Namely, an antibody-bonded liposome has been proposed.

Also in the field of cancer treatment, anti-cancer drug-containing antibody-bonded liposomes have been prepared, and many research institutes have reported excellent antitumor effects thereof (Konno et al., Cancer Res. 47, 4471 (1987), Hashimoto et al., Japanese Unexamined Patent Publication No. 134032/1983). However, at the same time, some problems of antibody-bonded liposomes have been pointed out. Namely, many of antibody-bonded liposomes administered are likely to be captured by organs of reticuloendothelial system such as liver and spleen, whereby no adequate effects tend to be obtained (Hashimoto et al., Cancer Res. 43 5328 (1983)).

On the other hand, it has been proposed to bond e.g. polyethylene glycol to a liposome as a method of improving the general properties of a liposome, such as leakage of the contained substance, agglomeration and a nature of being captured by organs of reticuloendothelial system (Japanese Unexamined Patent Publications No. 249717/1989 and No. 149512/1990, Alexander L. Klibanov et al, FEBS letters 268 235 (1990)).

However, in these methods, lipophilic derivatives of polyethylene glycol and a compound such as a long chain aliphatic acid are mixed with other liposome-constituting lipids, and a polyethylene glycol layer is formed on the liposome surface during the preparation of the liposome, or polyethylene glycol derivatives reactive with amino groups are attached to amino groups introduced to the liposome surface. When such methods are applied to an antibody bonded liposome, bonding of the antibody is likely to be hindered by the polyethylene glycol layer already formed on its surface, or deactivation of the antibody is likely to result. Therefore, the conventional method of incorporating polyethylene glycol has not been primarily intended for application to an antibody-bonded liposome.

The present inventors have conducted extensive studies to present a drug-containing antibody-bonded liposome having the nature of being captured in the reticuloendothelial system improved, and as a result, have found it possible to accomplish this object by firstly reacting a protein to which a thiol group is imparted (a thiol modified protein) to a liposome having maleimide groups and then reacting a compound having a moiety of a polyalkylene glycol to which a thiol group is imparted (a thiol-modified polyalkylene glycol) to the remaining maleimide groups.

Thus, the present invention provides a drug-containing protein-bonded liposome comprising a liposome containing a drug and having maleimide residues on its surface, and a protein and residues of a compound having a polyalkylene glycol moiety, bonded via respective thiol groups to the maleimide residues.

In the accompanying drawings:

FIG. 1 shows the reactivities of antibody-bonded liposomes to human gastric cancer cell line MKN 45, with respect to polyethylene glycol (PEG)-modified and non-modified liposomes.

The ordinate represents the amount bonded to MKN 45 in terms of the amount of 6-carboxyfluorescein (CF). In this Figure, lip represents the CF-loaded liposome, and antibody-bonded lip represents the CF-loaded antibody-bonded liposome.

Figure 2:
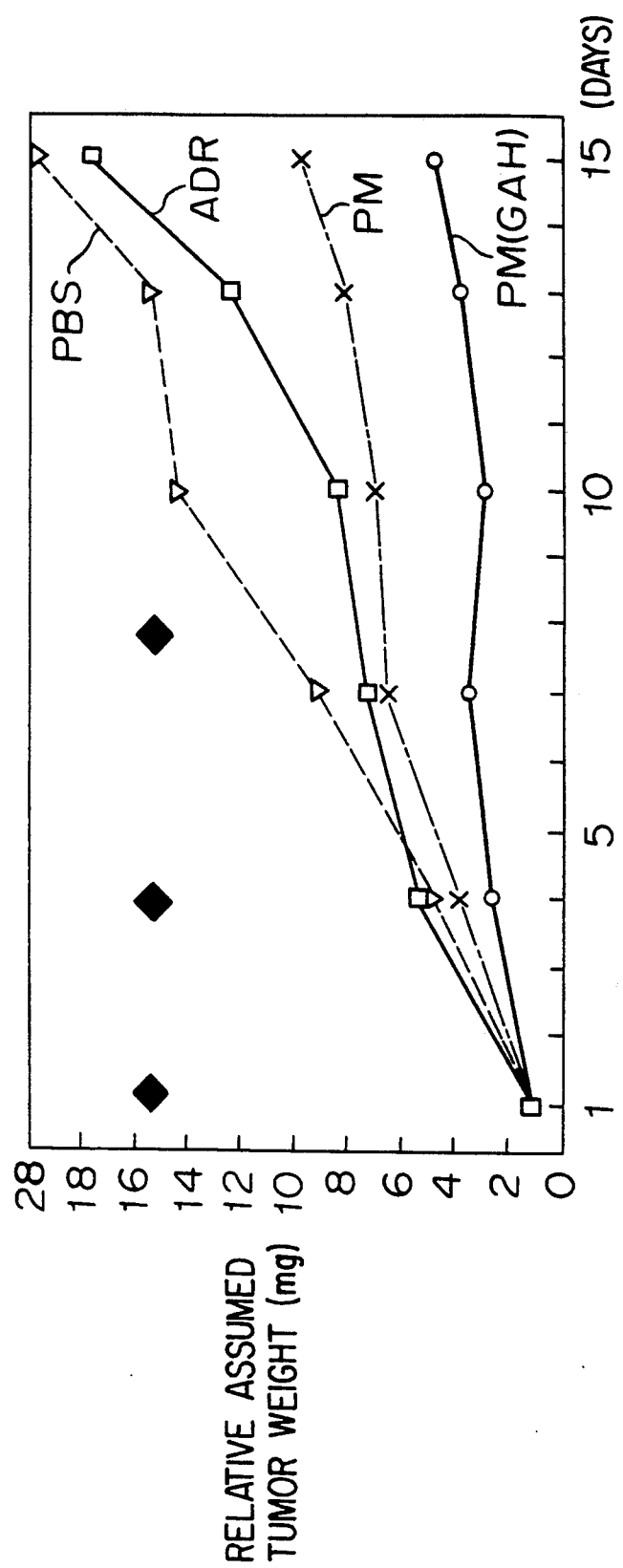

FIG. 2 shows the antitumor activities of the adriamycin-containing antibody-bonded PEG-modified liposome against cancer transplanted to nude mouse. The abscissa represents the number of days after initiation of the therapeutic test, and the ordinate represents the assumed tumor weight. In this Figure, ◆ represents the day on which the drug was administered; PBS represents a phosphate buffer physiological saline; ADR represents adriamycin alone; PM represents the adriamycin-containing PEG-modified liposome, and PM(GAH) represents the adriamycin-containing human monoclonal antibody-bonded PEG-modified liposome.

Now, the present invention will be described in detail with reference to the preferred embodiments.

(1) Liposome

① The liposome is composed essentially of phosphatidyl choline, cholesterol and maleimide-modified phosphatidyl ethanolamine. However, a phosphatidic acid such as dipalmitoylphosphatidic acid (DPPA) or the like may be incorporated as a substance imparting an electric charge.

As a preferred liposome, a liposome composed of dipalmitoylphosphatidyl choline (DPPC), cholesterol (Chol) and maleimide-modified dipalmitoylphosphatidyl ethanolamine (maleimide-modified DPPE), may be mentioned.

② The maleimide-modified phosphatidyl ethanolamine can be obtained by the reaction of a maleimide-containing compound reactive with an amino group, with an amino group of phosphatidyl ethanolamine (PE). The maleimide-containing compound may be N-($\epsilon$-maleimidocaproyloxy)succinimide, N-succinimidyl 4-(p-maleimidophenyl)butyrate, N-succinimidyl 4-(p-maleimidophenyl)propionate or N-($\gamma$-maleimidobutylyloxy)succinimide. PE may be dipalmitoylphosphatidyl ethanolamine.

③ The respective components are used in such proportions that per mol of the phosphatidyl choline, cholesterol is used in an amount of from 0.3 to 1 mol, preferably from 0.4 to 0.6 mol, the maleimide-modified phosphatidyl ethanolamine is used in an amount of from 0.01 to 0.2 mol, preferably from 0.02 to 0.1 mol, and the phosphatidic acid is used in an amount of from 0 to 0.4 mol, preferably from 0 to 0.15 mol.

④ For the preparation of the liposome, a conventional method can be used. For example, a lipid mixture having a solvent removed, is hydrated and emulsified by a homogenizer, followed by freezing-thawing to obtain a multilamella liposome. To further adjust it to a proper particle size, it may be subjected to supersonic treatment, high speed homogenizing or press-filtration by a membrane having uniform pores (Hope M. J. et al., Biochimica et Biophysica Acta 812, 55 (1985)).

A preferred size of the liposome is not larger than 300 nm, more preferably from 30 to 200 nm.

(2) Drug

① As the drug, an antitumor drug such as adriamycin, daunomycin, mitomycin, cisplatin, vincristine, epirubicin, methotrexate, 5FU or aclacinomycin, an aminoglucoside such as gentamicin, a $\beta$-lactam antibiotic such as sulpenisillin, a toxin such as ricin A or diphtheria toxin, antisense RNA against HIV or ras gene, or actinoplane (Polycyclic xanthones produced from actinoplane R-304 (K. Kobayashi et al., J. Antibiotics 41, 741 (1988)), may be employed.

② Loading of the drug into the liposome can he conducted by hydrating the lipid with an aqueous drug solution in the case of a water-soluble drug, or by mixing the drug and the lipid in a volatile organic solvent, followed by distilling the solvent off and hydrating the mixture of the drug and the lipid to embed the drug in the liposome, in the case of a fat-soluble drug. Further, in the case of adriamycin, daunomycin or epirubicin, loading can be conducted by a remote loading method utilizing a pH gradient (Lawrence D. Mayer et al., Cancer Res. 49, 5922 (1989)).

(3) Thiol-Modified Protein

① As the protein bonded to the liposome, various physiologically active substances including an antibody, FGF and EGF, may be employed. Preferred is an antibody. The antibody is an antibody reactive with the virus, bacteria, cells or tissue to be treated. For example, polyclonal antibodies of various animals, a mouse monoclonal antibody, a human-mouse chimeric antibody and a human monoclonal antibody may be employed. Among them, a human monoclonal antibody is preferred in the sense that it is not a protein of a foreign animal.

② Introduction of thiol groups to the protein can be conducted by a method wherein a compound is employed which is commonly used for thiol-modification of a protein and which is reactive with an amino group of the protein, such as N-succinimidyl-3-(2-pyridyldithio)propionate (SPDP) (Carlsson, J. et al., Biochem. J. 173, 723 (1978)) or iminothiolane, mercaptoalkylimidate (Traut, R. R. et al., Biochemistory 12, 3266 (1973)), or the like. In the case of an antibody, a method may be employed wherein endogenous dithiol groups are reduced to thiol groups. For bonding an antibody and a liposome, the latter method utilizing endogenous thiol groups is preferred from the viewpoint of the maintenance of the activities. When IgG is employed, it is subjected to F(ab')$_2$ modification with an enzyme such as pepsin, followed by reduction with e.g. dithiothreitol to obtain Fab', whereupon thiol groups formed in Fab' are subjected to the bonding reaction with the liposome (Martin, F. J. et al., Biochemistory, 20, 4229 (1981)). In the case of IgM, J-chain is reduced under a mild condition in accordance with a method of Miller et al. (J. Biol. Chem. 257, 286 (1965)), whereupon thiol groups of Fc moiety of IgMs thereby obtained, are subjected to the bonding reaction with the liposome.

③ Bonding of the maleimide group-containing liposome and the thiol-modified protein can be accomplished by reacting them in a neutral buffer solution (pH 6.5 to 7.5) for from 2 to 16 hours.

(4) Compound Containing a Thiol-Modified Polyalkylene Glycol Moiety

① As the polyalkylene glycol moiety of the compound, polyethylene glycol or polypropylene glycol may, for example, be mentioned. Preferred is polyethylene glycol, and its degree of polymerization is preferably from 20 to 400.

② To introduce thiol groups to polyalkylene glycols, various thiol-modification reactions which are commonly used for hydroxyl groups, amino groups, carboxyl groups and triazine, may be employed. Specific examples will be given below with respect to the case of polyethylene glycol, but it should be understood that the present invention is by no means restricted by such specific examples.

Namely, there are a method wherein monomethoxypolyoxy ethyleneamine and various thiolcarboxylic acids are dehydrated and condensed, a method wherein pyridyl dithiopropionyl group is introduced into monomethoxypolyoxy ethyleneamine by SPDP, followed by reduction, a method wherein thiol is introduced into monomethoxypolyoxy ethyleneamine by iminothiorane, a method wherein various thiolamines are bonded to active esters of monomethoxypolyoxy ethylenecarboxylic acid, and a method wherein a polyethylene glycol triazine derivative is bonded to thiolamine.

More specifically, as shown in the following Example, 2,4-bis(polyethylene glycol)-6-chloro-s-triazine (activated PEGII, manufactured by Seikagaku Kogyo K.K.) is reacted with cysteine, followed by reduction to obtain a cysteine-bonded activated PEGII.

(5) Supporting the Thiol-Modified Protein and the Compound Containing the Thiol-Modified Polyalkylene Glycol Moiety on the Surface of the Liposome To bond the thiol-modified protein and the compound containing the thiol-modified polyalkylene glycol moiety to the surface of the liposome, firstly, the thiol-modified protein is added and reacted in a neutral buffer solution to the liposome having an excess amount of maleimide groups. For example, in the case of a thiol-modified antibody, the thiol-modified antibody is employed in an amount of from 0.1% mol to 20% mol per mol of maleimide groups. Then, to the remaining maleimide groups, an excess amount of the thiol-modified polyalkylene glycol, preferably in an amount of at least twice in equivalent, is added to obtain an antibody-bonded polyalkylene glycol-modified liposome. By this process, it is possible to accomplish the blocking effects of excess remaining maleimide groups.

(6) Method of Use of the Drug-Containing Protein-Bonded Liposome

The drug-containing protein-bonded liposome thus obtained, such as an adriamycin-containing antibody-bonded PEG-modified liposome, may be formulated into a drug by a conventional method such as a dehydration method (Japanese PCT Publication No. 502348/1990), a method wherein a stabilizer is added to form a liquid formulation (Japanese Unexamined Patent Publication No. 9331/1989) or a freeze-drying method (Japanese Unexamined Patent Publication No. 9931/1989).

The drug thus formulated can be used by e.g. intravascular administration or local administration such as intravesical or intraperitoneal administration against various diseases including cancer. The administration amount may be optionally selected depending on the drug contained in liposome.

In the case of an adriamycin-containing liposome, as an example, the dose is usually at most 50 mg/kg, preferably at most 10 mg/kg, more preferably at most 5 mg/kg, as the amount of adriamycin.

Now, the present invention will be described in further detail with reference to Examples. However, it should be understood that the present invention is by no means restricted to such specific Examples.

EXAMPLE 1

Confirmation of the Effect Whereby PEG-Modified Adriamycin-Containing Liposome Avoids he Reticuloendothelial System Preparation of Thiol-Modified Polyethylene Glycol 48 mg of L-cysteine was dissolved in a 0.4M boric acid buffer solution. Then, 200 mg of 2,4-bis(polyethyleneglycol)-6-chloro-s-triazine (activated PEGII, manufactured by Seikagaku Kogyo K.K.) was added thereto, and the mixture was reacted at room temperature overnight. To the cysteine-bonded PEG thus obtained, 62 mg of dithiothreitol (DTT) was added, and the mixture was reacted at 37° C. for 6 hours to obtain a solution containing a cysteine-bonded PEG. The reaction solution was further desalted by gel filtration on GH-25 column (manufactured by Seikagaku Kogyo K.K.), and the solvent was replaced by 10 mM phosphate buffer solution pH7.4 and 0.15M NaCl (PBS). Then, the solution was added to 7 ml of thiopropylsepharose 6B (Pharmacia) equilibrated with PBS. Non-bonded substance was removed by washing with PBS. The cysteine-bonded PEG bonded to the gel was eluted with PBS containing 50 mM DTT. Then, excess DTT was removed by gel filtration to obtain the above-identified product.

Preparation of Maleimide-Modified Dipalmitoylphosphatidyl Ethanolamine 127 mg of dipalmitoylphosphatidyl ethanolamine, 80 mg of N-(ε-maleimidocarproyloxy) succinimide (EMCS) and 44 ul of triethylamine were added to a chloroform solution containing 1/5 of methanol and reacted under a nitrogen stream. Three hours later, 20 mg of EMCS was further added, and the mixture was further reacted at room temperature for 3 hours.

After confirming that the ninhydrin reaction of the reaction solution became negative, the reaction solution was evaporated to dryness under reduced pressure, and the product was dissolved again in a small amount of chloroform.

The maleimide-modified dipalmitoylphosphatidyl ethanolamine was purified by chromatography using UNISIL (manufactured by Gaschro Kogyo K.K.). Namely, the product was added to the column equilibrated with chloroform and developed with an eluting solution of chloroform/methanol=10/1 to obtain the desired substance.

Preparation of Maleimide-Containing Adriamycin-Loaded Liposome 1 ml of a 0.3M citric acid buffer solution pH4 was added to 100 mg of a solid lipid mixture of DPPC/chol/DPPA/maleimide-modified DPPE=18/10/2/0.5 (mol ratio) (manufactured by Nippon Seika K.K.), and the mixture was stirred. Then, freezing-thawing was repeated five times for hydration to obtain a multi-lamella liposome. Then, the multi-lamella liposome was subjected to press-filtration ten times while heating at 60° C. by a press apparatus (extruder, manufactured by Lipex Biomembranes) provided with a polycarbonate membrane having a pore size of 200 nm (nucleopore, Microscience), to obtain a liposome having a regulated particle size. This liposome solution was neutralized with a 1M NaOH solution. While heating the liposome solution at 60° C., adriamycin (manufactured by Kyowa Hakko) was added in an amount of 1/10 by weight of the lipid. At least 97% of adriamycin was actively loaded to the liposome in accordance with the pH gradient between the interior and exterior of the liposome, to obtain a maleimide-containing adriamycin loaded liposome.

Introduction of Thiol-Modified PEG to the Maleimide-Containing Liposome

To the above maleimide-containing liposome, 5 μmol of thiol-modified PEG was added, and the mixture was reacted in PBS at room temperature for 6 hours to obtain a PEG-modified adriamycin-loaded liposome. Further, the liposome was subjected to gel filtration by sepharose CL6B (pharmacia) to separate unreacted cysteine-bonded PEG, followed by evaluation test.

Study of Intracorporeal Behavior

The prepared liposome was intravenously administered to a mouse from the tail in an amount of 5 mg/kg as adriamycin, and 30 minutes later, the mouse was killed, and adriamycin in each of the extracted organs was extracted and quantitatively analyzed in accordance with the method of Konno et al.

Namely, each organ was homogenized in a 0.3M hydrochloric acid, 50% ethanol, heated and centrifugally separated, whereupon the supernatant was measured by fluorescence of Ex 490 nm and Em 590 nm.

As shown in Table 1, a decrease in the amount of adriamycin in the liver and spleen was observed, and maintenance of a high concentration in the blood was observed.

TABLE 1

Concentration of adriamycin in the respective organs upon expiration of 30 minutes from the administration (ug/g tissue)

|  | free ADR | lip = ADR | PEG-lip = ADR |
| --- | --- | --- | --- |
| Blood | 0.2 | 8.7 | 17.8 |
| Liver | 18.2 | 31.8 | 17.2 |
| Spleen | 7.2 | 110.1 | 90.6 |
| Lung | 7.9 | 4.2 | 5.5 |
| Heart | 3.2 | 1.5 | 3.5 |

TABLE 1-continued

Concentration of adriamycin in the respective organs upon expiration of 30 minutes from the administration (ug/g tissue)

| | free ADR | lip = ADR | PEG-lip = ADR |
|---|---|---|---|
| Reu | 1.4 | 0.3 | 0.5 |
| Brain | 0 | 0.1 | 0.3 |

EXAMPLE 2

Confirmation of the Reactivity of the Antibody-Bonded PEG-Modified Liposome 1 ml of a 0.1M 6-carboxyfluorescein as a fluorescent marker was added to 100 mg of a solid lipid mixture (manufactured by Nippon Seika) of DPPC/chol/maleimide-modified DPPE=18/10/0.5 (mol ratio), and the mixture was hydrated and the particle size adjusted in the same manner as in Example 1 to obtain a maleimide-containing fluorescent dye-loaded liposome.

Preparation of a Thiol-Modified Antibody

To an antitumor mouse monoclonal antibody (I9G), 1/40 mol amount of pepsin (Cooper Biomedical) in 0.1M acetic acid buffer solution pH 3.5, was added, and the mixture was reacted at 37° C. overnight for digestion to obtain F(ab')$_2$. Further, by chromatography separation with a cationic exchange resin (mono S, manufactured by Pharmacia), F(ab')$_2$ was isolated. The separation was conducted by a linear gradient of from 0M to 1.0M NaCl in a 0.1M acetic acid buffer solution pH4.0.

To reduce it to Fab', 12 ul of 10% DTT was added per mg of the antibody in a 0.1M acetic acid buffer solution containing 0.15M NaCl (pH 4.5), and the mixture was left to stand at room temperature for 80 minutes. After completion of the reaction, demineralization was conducted by gel filtration on PD-10 column (manufactured by Pharmacia) equilibrated with PBS to obtain Fab'. To the liposome obtained from 100 mg of the above lipid, 5 mg of Fb' was added, and the mixture was reacted at 37° C. for 8 hours and further 5 umol of thiol-modified polyethylene glycol was added to react it with excess maleimide, to obtain an antibody-bonded PEG-modified liposome.

Confirmation of the Bonding Activity of the PEG-Modified Antibody-Bonded Liposome Using human gastoric cancer cell line MKN 45, of which the reactivity of the used monoclonal antibody had been confirmed, the reactivity of the PEG-modified antibody bonded liposome was confirmed in vitro.

The above carboxyfluorescein-loaded antibody-bonded PEG-modified liposome was added to $8 \times 10^5$ cells of MKN 45 floated in trypcin, and the mixture was reacted in 90% human inactivated serum at 37° C. for 230 minutes. The centrifugal pellet of cells was washed with PBS, and then carboxyfluorescein was freed at 60° C. with 10% triton $\times$ 100, and the amount bonded to the cells was calculated by a fluorescence measurement.

As shown in FIG. 1, a high reactivity with the objective cells was observed also in the case of the antibody-bonded PEG-modified liposome.

EXAMPLE 3

Confirmation of the Pharmacological Activities of the Adriamycin-Loaded Monoclonal Antibody-Bonded PEG-Modified Liposome A solid lipid mixture of DPPC/chol/maleimide-modified DPPE=18/10/0.5 (mol ratio) was treated in the same manner as in Example 1 to obtain an adriamycin-loaded maleimide-containing liposome.

Using a human monoclonal antibody (IgG), Fab'-modified antibody was obtained in the same manner as in Example 2 except that the pH for the pepsin digestion was changed to 4.0, and it was subjected to the bonding with the liposome. Further, it was modified by thiol-modified PEG in the same manner to obtain an adriamycin-loaded human monoclonal antibody-bonded PEG-modified liposome.

Evaluation of the Pharmacological Activities Using A Human Gastric Cancer Cell Line-Transplanted Nude Mouse System Using human cancer cell line MKN 45 of which the reactivity with the antibody was observed in vitro, and accumulation was observed in vivo with respect to the nude mouse-transplanted system, the antitumor activities were studied.

For a therapeutic test, $1 \times 10^6$ cells of MKN 45 cultured, were subcutaneously transplanted to a nude mouse, and the therapeutic test was initiated when the weight of the tumor became about 100 mg ten days later. On the first day, the fourth day and the ninth day from the initiation of the therapy, the liposome was intravenously administered to the mouse from the tail in an amount of 5 mg/kg as adriamycin. To measure the change with time of the proliferation of the tumor, an assumed tumor weight was obtained by a calculation formula of short diameter $\times$ short diameter $\times$ long diameter/2 of the tumor in accordance with a Battelle Columbus method, and the change with time was shown using as a reference the weight of the tumor at the initiation of the therapy.

As a result, as shown in FIG. 2, strong antitumor activities of the adriamycin-loaded monoclonal antibody-bonded PEG-modified liposome were shown.

With the liposome obtained by the present invention, it is possible to suppress the non-specific capture in the reticuloendothelial system such as liver or spleen as observed with the conventional liposomes, and thus the liposome of the present invention is effective for use as a selective chemotherapeutic drug, particularly as a cancer treating drug.

We claim:

1. A drug containing, protein-bonded liposome, which comprises a liposome containing a drug, said liposome having maleimide groups on the surface thereof, wherein a portion of the maleimide groups are bonded to a thiol group-containing protein and a remaining portion of the maleimide groups are bonded to a thiol group-containing polyethylene glycol moiety; said liposome comprising phosphatidyl choline, cholesterol and maleimide-modified phosphatidyl ethanolamine.

2. The drug-containing, protein-bonded liposome of claim 1, wherein the protein is selected from the group consisting of an antibody, FGF and EGF.

3. The drug-containing, protein-bonded liposome of claim 2, wherein said protein is an antibody selected from the group consisting of animal polyclonal antibodies, mouse monoclonal antibodies, human-mouse chimeric antibodies and human monoclonal antibodies.

4. The drug-containing, protein-bonded liposome of claim 3, wherein said protein is a human monoclonal antibody.

5. The drug-containing, protein-bonded liposome of claim 1, wherein the liposome comprises dipalmitoylphosphatidyl choline, cholesterol and maleimide-modified dipalmitoylphosphatidyl ethanolamine.

6. The drug-containing, protein-bonded liposome of claim 5, wherein the maleimide-modified dipalmitoylphosphatidyl ethanolamine is obtained by reacting N-($\epsilon$-maleimidocaproyloxy) succinimide and dipalmitoylphosphatidyl ethanolamine.

7. The drug-containing, protein-bonded liposome of claim 1, wherein the thiol group-containing protein having maleimide groups bonded thereto is obtained by reacting maleimide residues on the liposome surface and a thiol group-containing protein.

8. The drug-containing, protein-bonded liposome of claim 1, wherein said thiol-group containing polyethylene glycol moiety having maleimide groups bonded thereto is obtained by reacting maleimide residues on the liposome surface and a thiol-group containing polyethylene glycol.

9. The drug-containing, protein-bonded liposome of claim 1, wherein said drug comprises an antitumor drug, a $\beta$-lactam antibiotic, a toxin, an aminoglucoside, antisense RNA or actinoplane.

10. The drug-containing, protein-bonded liposome of claim 9, wherein the antitumor drug is selected from the group consisting of adriamycin, daunomycin, mitomycin, cisplatin, vincristine, epirubicin, methotrexate, 5-FU and aclacinomycin.

11. The drug containing, protein-bonded liposome of claim 9, wherein said aminoglucoside is gentamicin.

12. The drug containing, protein-bonded liposome of claim 9, wherein said $\beta$-lactam antibiotic is sulpenisillin.

13. The drug containing, protein-bonded liposome of claim 9, wherein said toxin is ricin A or diphtheria toxin.

14. The drug containing, protein-bonded liposome of claim 9, wherein said antisense RNA is antisense RNA against HIV or ras gene.

15. An antitumor drug, comprising a liposome containing a drug, said liposome having maleimide groups on the surface thereof, wherein a portion of the maleimide groups are bonded to a thiol group-containing protein and a remaining portion of the maleimide groups are bonded to a thiol group-containing polyethylene glucol moiety; said liposome comprising phosphatidyl choline, cholesterol and maleimide-modified phosphatidyl ehtanolamine.

* * * * *